US00PP35806P2

(12) United States Plant Patent
DeVries

(10) Patent No.: US PP35,806 P2
(45) Date of Patent: May 14, 2024

(54) ***ILEX* PLANT NAMED 'DD-21'**

(50) Latin Name: *Ilex verticillata*
Varietal Denomination: DD-21

(71) Applicant: Leendert DeVries, Arcata, CA (US)

(72) Inventor: Leendert DeVries, Arcata, CA (US)

( * ) Notice: Subject to any disclaimer, the term of this patent is extended or adjusted under 35 U.S.C. 154(b) by 0 days.

(21) Appl. No.: 17/803,718

(22) Filed: Oct. 27, 2022

(51) Int. Cl.
*A01H 5/00* (2018.01)
*A01H 6/00* (2018.01)

(52) U.S. Cl.
USPC ..... Plt./247

(58) Field of Classification Search
USPC ..... Plt./247
See application file for complete search history.

*Primary Examiner* — Susan McCormick Ewoldt
(74) *Attorney, Agent, or Firm* — Samuel R. McCoy, Jr.

(57) ABSTRACT

A new and distinct *Ilex verticillata* plant named 'DD-21' which is characterized by vigorous growth, an abundance of strong upright main stems, short lateral branches with each bearing an abundance of very large vibrant red berries borne along their entire length. The claimed plant propagates successfully by softwood stem cuttings and has proven to be uniform and stable in the resulting generations.

1 Drawing Sheet

Latin name of the genus and species: The Latin name of the genus and species of the novel variety disclosed herein is *Ilex verticillata.*

Variety denomination: The inventive variety of *Ilex verticillata* disclosed herein has been given the variety denomination 'DD-21'.

BACKGROUND OF THE INVENTION

The present invention relates to a new and distinct variety of *Ilex verticillata*, which has been given the denomination, 'DD-21'. *Ilex verticillata*, known commonly as winterberry, is a deciduous perennial that is widely cultivated for its ornate berries born along the lateral branches. The berries persist for many months through fall and winter, making it an ideal plant for ornamental landscaping in its hardiness range and also for the cut flower industry.

Parentage: The new cultivar 'DD-21' is a seedling selection resulting from the open pollination of *Ilex verticillata* 'Magical Times' (not patented), the seed parent, and an undesignated male *Ilex verticillata* plant, the pollen parent. In 2010, seeds were harvested from 'Magical Times' which resulted in approximately 2,000 seedlings. In March of 2006, the seedlings were transplanted into a field in Willow Creek, California and grown to a mature size. From 2006 to 2016, these plants were evaluated for commercial production, based on criteria such as growth habit and fruiting habit. In the fall of 2016, one plant was observed which exhibited an abundance of main stems bearing very large, vibrant red berries borne all along the short lateral branches and berries which matured earlier than the parents and other progeny. This new plant was given the breeder denomination, 'DD-21'.

Asexual Reproduction: In the summer of 2017, 'DD-21' was first asexually reproduced in Willow Creek, California by way of softwood stem cuttings taken from one year old growth. The claimed plant was found to asexually reproduce in uniform and stable manner and two successive cycles of vegetative propagation have proven to be true to type.

SUMMARY OF THE INVENTION

The following characteristics have been repeatedly observed and represent the distinguishing characteristics of the new *Ilex verticillata* cultivar 'DD-21'. These traits, in combination, distinguish 'DD-21' as a new and distinct cultivar.

1. 'DD-21' exhibits excellent plant vigor and a fast rate of growth; and
2. 'DD-21' exhibits an abundance of strong and upright main stems; and
3. 'DD-21' exhibits short lateral branches; and
4. 'DD-21' exhibits a large quantity of berries born along the entire length of the lateral branches, including the distalmost portion of the lateral branches usually devoid of berries in the species, which negates the need for manual pruning or use of plant growth regulators; and
5. 'DD-21' exhibits very large, vibrant red berries.

BRIEF DESCRIPTION OF THE FIGURES

The figure illustrates, as nearly true as it is reasonably possible to make the same in color photographs of this type, an exemplary 4.5-year-old field-grown 'DD-21' plant in Willow Creek, California.

BOTANICAL DESCRIPTION OF THE PLANT

The following is a detailed botanical description of a new and distinct variety of a *Ilex verticillata* known as 'DD-21'. Plant observations were made on field grown plants produced in Willow Creek, California. Unless indicated otherwise, the descriptions disclosed herein are based upon observations made of a mature 'DD-21' plant, transplanted into a loamy clay field on May 1, 2018, as a one-year-old rooted cutting grown in a 4-inch nursery pot. The plant was grown in full sun and was provided a combination of overhead and drip irrigation. Fertilizer was regularly applied using a fertigation technique, and the plant was occasionally treated for mites when required. In March of 2019 and again in the fall of 2020, the plant was pruned to 7 cm above soil level and have since been allowed to grow without further pruning. Observation data was recorded in early October of 2022.

Those skilled in the art will appreciate that certain characteristics will vary with older or, conversely, younger plants. 'DD-21' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, 1986 edition except where common terms of color are used.

A botanical description of 'DD-21' and comparisons with the seed parent and most similar commercial variety known to the inventor are provided below.

General plant description:

*Plant habit*.— Deciduous perennial shrub with an upright growth habit and excellent plant vigor.

*Height*.—Approximately 165 cm.

*Width*.—Approximately 120 cm.

*Environmental tolerances*.—Hardy in US Hardiness Zones 3 through 9; high tolerance to wind and rain.

*Pest and disease susceptibility or resistance*.—Plants have not been observed to be susceptible or resistant to pathogens and pests common to *Ilex verticillata*.

*Propagation*.—Propagation is accomplished using softwood stem cuttings.

*Time to develop roots*.—Approximately 21 days, in a propagation house with bottom heat and an average ambient temperature of 25 degrees Celsius.

*Crop time*.—Approximately 5 weeks are needed to produce a fully rooted cutting; after transplanting young plants grown in four-inch nursery containers into a production field, fruit bearing stems can be harvested from the mature plants at the end of the second growing season.

Root system:

*Description*.—A network of larger primary roots and fine, fibrous lateral roots.

*Rooting habit*.—Freely branching, dense, and evenly distributed throughout the soil profile.

*Color, primary roots*.—Nearest to a mixture of greyed-yellow, greyed-orange, and greyed-brown; RHS 161A, 165A, and 199A.

*Color, lateral roots*.—Greyed-orange, nearest to RHS 165C.

Stems:

*Branching habit*.—Free, basally branching habit; numerous upright main stems, each producing numerous lateral branches. Main stems are typically unbranched, yet occasionally branched. Main stems — Quantity — 38, on average. Attitude — Erect; near vertical. Cross section — Circular. Diameter — An average of 11.5 mm, at the base of the most mature stems. Length — 130.4 cm, on average. Internode length — Varying from 10 to 20 mm. Color — Nearest to a mixture of yellow-green and greyed-green, RHS 148A, 197A, and 197B, with densely reticulated fissures; fissures are colored greyed-brown, nearest to RHS 199D. Texture — Glabrous and fissured; lenticels present. Lenticels are elliptical; approximately 1.0 mm long and 0.5 mm wide; lenticel color is greyed-brown, nearest to RHS 199D. Strength — Very strong. Lateral branches — Quantity — Many of the lower lateral branches senesce with age, with only a few very short lateral branches present, proximally; 18 to 27 lateral branches per main stem which are predominantly present on the upper two-thirds of main stems. Stem angle to main axis — In between 50 and 70 degrees. Cross-section — Circular. Diameter — 2.5 mm at the base. Length — Ranging from 8.0 mm, distally, to as long as 65 mm; 53.5 mm on average. Internode length — Varying from 10 to 15 mm. Color, juvenile — Yellow-green, RHS 144A. Color, mature — Nearest to a mixture of yellow-green and greyed-green; RHS 144A, 147B, 199B, and 199C. Texture — Smooth, glabrous; lenticels present. Lenticels are elliptical; approximately 1.0 mm long and 0.75 mm wide; color is greyed-brown, RHS 199D. Stem strength — Strong.

Foliage:

*Arrangement*.—Alternate.

*Attachment*.—Petiolate.

*Division*.—Simple.

*Shape*.—Elliptical.

*Length*.—50.2 mm, on average.

*Width*.—23.0 mm, on average.

*Apex*.—Acuminate.

*Base*.—Cuneate.

*Margin*.—Serrate; slightly undulated.

*Aspect*.—Nearly flat to concave.

*Texture and pubescence, adaxial surface*.—Glabrous and slightly rugose.

*Texture and pubescence, abaxial surface*.—Glabrous and slightly rugose.

*Color*.—Juvenile foliage, adaxial surface — Yellow-green, nearest to RHS 147A. Juvenile foliage, abaxial surface — Yellow-green, nearest to RHS 147B. Mature foliage, adaxial surface — Nearest to in between yellow-green and green, RHS 147A and 137B yet nearest to 137B. Mature foliage, abaxial surface — Nearest to in between yellow-green and green, RHS 147C and 138B yet nearest to 138B.

*Venation*.—Pattern — Pinnate. Vein color, adaxial surface — Yellow-green, RHS 145B. Vein color, abaxial surface — Yellow-green, RHS 145B.

*Petiole*.—Length — 12.4 mm, on average. Diameter — 1.5 mm, on average. Color, adaxial surface — Yellow-green, RHS 145A. Color, abaxial surface — Yellow-green, nearest to RHS 145B. Texture, adaxial and abaxial surfaces — Smooth; glabrous.

Inflorescence:

*Type*.—Solitary flowers occur at the leaf axils, with 1 to 3 flowers at each axil.

Flower bud:

*Shape*.—Globose to short ovoid.

*Dimensions*.—2.75 mm long and 2.75 mm in diameter, on average.

*Color, upper and lower surfaces*.—Yellow-green, RHS 145B, at the base and becoming green-white towards the distal end, RHS 157C.

Flower:

*General description*.—Single rotate flowers with a shallow cup shape.

*Natural flowering season.*—May through early June in Willow Creek, California.

*Quantity.*—1 to 3 flowers per axil, with approximately 6 to 9 flowers on shorter proximal lateral branches and 18 to 36 on longer distal lateral branches.

*Lastingness.*—At greater than 25 degrees Celsius, petals drop away in approximately 5 days; at 15 degrees Celsius, petals drop away in approximately 8 days.

*Persistence.*—Not persistent.

*Fragrance.*—Not fragrant.

*Attitude.*—Flowers held upright and slightly outward.

*Dimensions.*—Corolla is 6.0 mm in diameter and 3.0 mm deep.

*Peduncle.*—Dimensions — 3.0 mm long and 0.75 mm in diameter. Color — Yellow-green, RHS 144B. Texture — Smooth; glabrous. Strength — Medium.

*Calyx.*—Shape — Sepals fused at the base forming a cup, with 6 rotate sepal lobes. Diameter — 2.25 to 2.5 mm, measured from apex of one sepal lobe to the apex of an opposing sepal lobe. Depth — 1.25 mm deep. Quantity of sepal lobes — 6 sepal lobes. Apex, sepal lobes — Sepal lobes acute. Base — Fused. Margin — Entire; ciliate. Texture, inner and outer surfaces — Smooth and glabrous. Color when opening, inner surface — Yellow-green, a mixture of RHS 144D and 145C. Color when opening, outer surface — Yellow-green, a mixture of RHS 144D and 145C. Color when fully open, inner surface — Yellow-green, a mixture of RHS 144D and 145C. Color when fully open, outer surface — Yellow-green, a mixture of RHS 144D and 145C.

*Petals.*—Quantity of petals — 6 petals, fused at the base. Arrangement — Single rotate whorl. Petal lobe apex — Obtuse. Petal lobe margin — Entire; slightly undulated. Texture, inner and outer surfaces — Smooth; glabrous. Luster, inner and outer surfaces — Matte to very slightly glossy. Color when opening, inner surface — White, RHS 155D. Color when opening, outer surface — White, RHS 155D. Color when fully open, dorsal surface — Nearest to white, RHS 155D; petals are slightly translucent. Color when fully open, ventral surface — Nearest to white, RHS 155D; petals are slightly translucent. Petal color fading to — Not fading.

Reproductive organs:

*Androecium.*—Stamens — Quantity — 0.6. Position — Inserted; free. Attachment — One stamen attached at the base of each petal. Overall length — Approximately 1.20 mm long. Filament — Dimensions — 0.5 to 0.75 mm long and approximately 0.25 mm in diameter. Color — White, nearest to RHS 155D. Anthers — Attachment — Basifixed. Shape — Nearly globose, with a longitudinal split. Dimensions — 0.5 mm long and 0.5 mm wide. Color — White, nearest to RHS 155D. Pollen — None.

*Gynoecium.*—Pistils — Quantity — One; inferior to the corolla. Overall dimensions — Approximately 2.0 mm tall and 1.75 mm in diameter at the widest point. Stigma — Shape — Globular. Dimensions — 1.5 to 1.75 mm in diameter, and 0.5 mm to 0.75 mm tall. Color — Yellow-green, approximating to a combination of RHS 144C and 144D. Style — Shape — Relatively broad, and truncated. Dimensions — 0.5 to 0.75 mm tall and 0.5 to 0.75 mm in diameter. Color — Yellow-green, nearest to a mixture of RHS 144B, 151A, and 151B. Ovary — Position — Superior. Dimensions — 0.5 to 0.75 mm tall and 1.0 mm in diameter. Color — Yellow-green, RHS 144C.

Fruit and seed:

*Fruit.*—Type — Simple, indehiscent berry. Time to maturity — Very early to fruit, maturing usually near the first week of September in Willow Creek, California. Shape — Globose. Quantity — 1 to 3 berries per axil, with approximately 6 to 9 berries on shorter proximal lateral branches and typically between 18 and 27 berries on longer distal lateral branches. Dimensions — Approximately 9.5 mm in diameter, and 9 mm tall. Texture, pubescence and luster — Smooth, glabrous and glossy. Color, mature fruit — Red, nearest to in between RHS 44A and 45B; berries do not fade with age.

*Seed.*—Quantity — Usually 4 per berry. Shape — Oblong, three-sided, with an ovate to deltoid outline. Dimensions — 3.5 to 4.0 mm long and 1.25 to 1.5 mm in diameter. Color — Greyed-orange, RHS 164C. Texture — Slightly rough.

COMPARISON WITH THE PARENT PLANTS

Plants of the new cultivar 'DD-21' differ from the seed parent, *Ilex verticillata* 'Magical Times' (not patented), by the characteristics described in Table 1. The pollen parent is unknown and therefore no comparison is available.

TABLE 1

| Characteristic | 'DD-21' | 'Magical Times' |
|---|---|---|
| Timing of fruit maturation. | Typically, by the first week of September in Willow Creek, California; one week earlier than 'Magical Times'. | Typically, in the second week of September; one week later than 'DD-21'. |
| Occurrence of berries on lateral branches. | Berries present along the entire length of lateral branches. | Berries only present on approximately 60 percent of lateral branches; distalmost portion devoid of berries. |
| Productivity; number of harvestable main stems. | 38 stems per plant, at maturity. | 10 to 12 stems per plant, at maturity. |

COMPARISON WITH THE MOST SIMILAR *ILEX VERTICILLATA* CULTIVAR KNOWN TO THE INVENTOR

Plants of the new cultivar 'DD-21' are most similar to the cultivar, 'Oosterwijk' (not patented). A comparison of 'DD-21' with *Ilex* 'Oosterwijk' is described in Table 2.

TABLE 2

| Characteristic | 'DD-21' | 'Oosterwijk' |
|---|---|---|
| Timing of fruit maturation. | Typically, by the first week of September in Willow Creek, California; one week earlier than 'Oosterwijk'. | Typically, in the fourth week of September; three to four weeks later than 'DD-21'. |
| Productivity; number of harvestable main stems. | 38 stems per plant, at maturity. | 8 to 12 stems per plant, at maturity. |
| Occurrence of berries on lateral branches. | Berries present along the entire length of lateral branches. | Berries only present on approximately 40 percent of lateral branches; distalmost portion devoid of berries. |

That which is claimed is:

1. A new and distinct variety of *Ilex verticillata* plant named 'DD-21', substantially as described and illustrated herein.

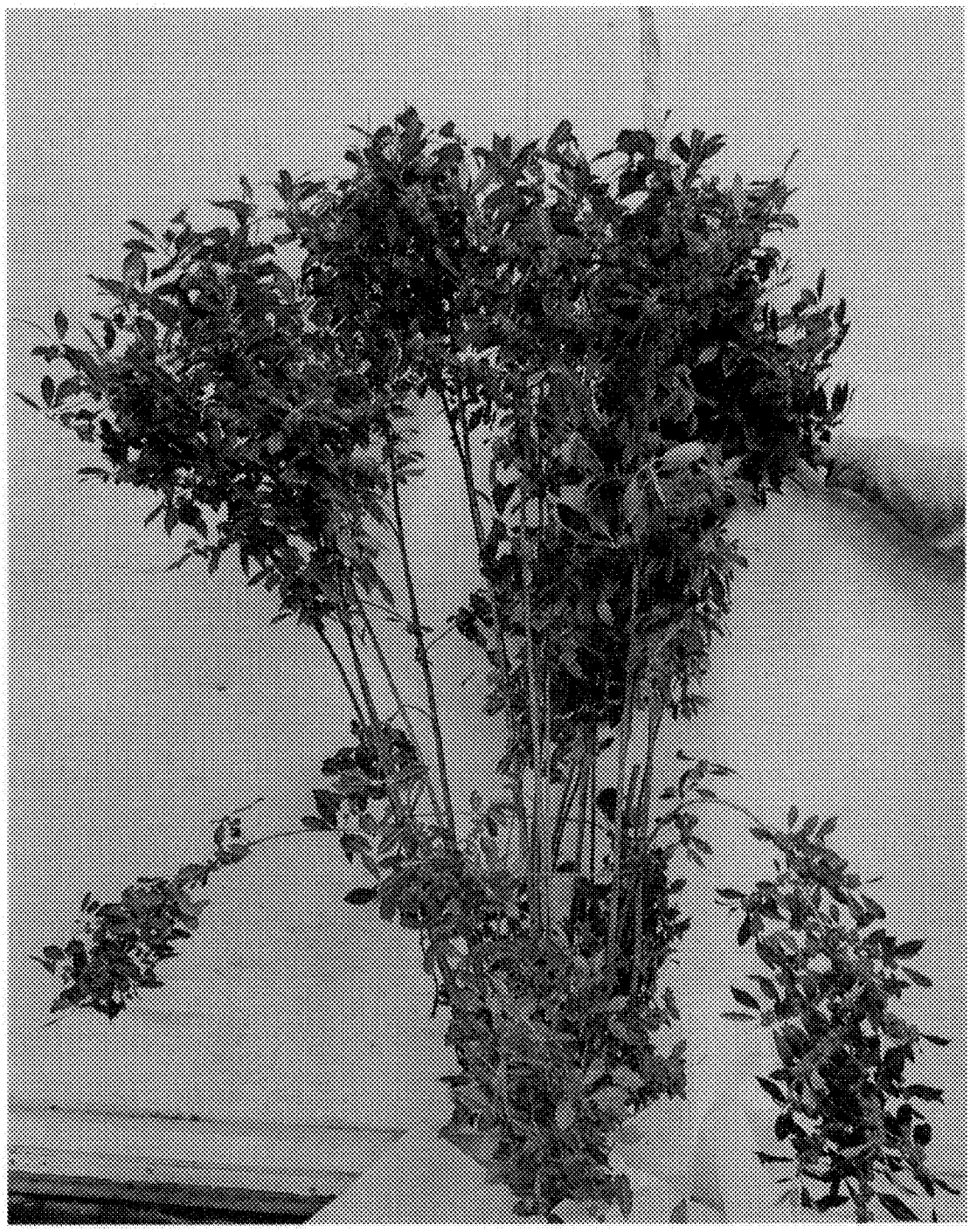

* * * * *